US009408531B2

United States Patent
Okada et al.

(10) Patent No.: US 9,408,531 B2
(45) Date of Patent: Aug. 9, 2016

(54) OPHTHALMOLOGIC APPARATUS

(71) Applicant: KABUSHIKI KAISHA TOPCON, Itabashi-ku (JP)

(72) Inventors: Hiroaki Okada, Saitama (JP); Taisaku Kogawa, Mitaka (JP); Takashi Fujimura, Fujimino (JP); Kohta Fujii, Toda (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 14/655,864

(22) PCT Filed: Dec. 4, 2013

(86) PCT No.: PCT/JP2013/082645
§ 371 (c)(1),
(2) Date: Jun. 26, 2015

(87) PCT Pub. No.: WO2014/103646
PCT Pub. Date: Jul. 3, 2014

(65) Prior Publication Data
US 2015/0335234 A1    Nov. 26, 2015

(30) Foreign Application Priority Data

Dec. 26, 2012  (JP) ................................. 2012-283742

(51) Int. Cl.
*A61B 3/14*    (2006.01)
*A61B 3/00*    (2006.01)
(Continued)

(52) U.S. Cl.
CPC .............. *A61B 3/0025* (2013.01); *A61B 3/0083* (2013.01); *A61B 3/102* (2013.01); *A61B 3/117* (2013.01); *A61B 3/12* (2013.01); *A61B 3/152* (2013.01); *A61B 3/154* (2013.01)

(58) Field of Classification Search
USPC ......... 351/200, 203, 204, 205, 206, 208, 209, 351/210, 211, 222, 223, 224, 243, 244, 245, 351/246
See application file for complete search history.

(56) References Cited

U.S. PATENT DOCUMENTS

2004/0156019 A1    8/2004   Masaki
2007/0299429 A1    12/2007  Amano
(Continued)

FOREIGN PATENT DOCUMENTS

EP    2 281 500 A1    2/2011
JP    05 56927        3/1993
(Continued)

OTHER PUBLICATIONS

International Search Report Issued Jan. 14, 2014 in PCT/JP2013/082645 filed Dec. 4, 2013.
(Continued)

*Primary Examiner* — Stephone B Allen
*Assistant Examiner* — Brandi Thomas
(74) *Attorney, Agent, or Firm* — Oblon, McClelland, Maier & Neustadt, L.L.P.

(57) ABSTRACT

An ophthalmologic apparatus includes an examination optical system, drive part, two or more imaging parts, analyzer, storage, position corrector, and controller. The examination optical system examines an eye. The drive part moves the examination optical system. The imaging parts substantially simultaneously photograph the anterior segment of the eye from different directions. The analyzer analyzes two or more photographic images captured substantially simultaneously by the imaging parts to obtain a three-dimensional position of the eye. The storage stores correction information in advance. The correction information is acquired based on optical properties of eyeballs, and used to correct the position of the eye in the optical axis direction of the examination optical system. The position corrector corrects the three-dimensional position obtained by the analyzer based on the correction information. The controller controls the drive part based on the three-dimensional position corrected to move the examination optical system.

12 Claims, 10 Drawing Sheets

(51) Int. Cl.
*A61B 3/117* (2006.01)
*A61B 3/15* (2006.01)
*A61B 3/10* (2006.01)
*A61B 3/12* (2006.01)

(56) References Cited

U.S. PATENT DOCUMENTS

| | | | |
|---|---|---|---|
| 2009/0190093 A1 | 7/2009 | Tanassi et al. | |
| 2010/0165293 A1 | 7/2010 | Tanassi et al. | |
| 2011/0063421 A1* | 3/2011 | Kubota | H04N 13/0003 348/52 |
| 2015/0085252 A1 | 3/2015 | Fujimura et al. | |
| 2015/0124069 A1* | 5/2015 | Tsukamoto | G06K 9/00604 348/78 |
| 2015/0286070 A1* | 10/2015 | Aikawa | G02C 7/025 351/159.76 |

FOREIGN PATENT DOCUMENTS

| | | |
|---|---|---|
| JP | 2001 046340 | 2/2001 |
| JP | 2005 287782 | 10/2005 |
| JP | 4136690 | 8/2008 |
| JP | 2009 112664 | 5/2009 |
| JP | 2010 012109 | 1/2010 |
| JP | 2011 507572 | 3/2011 |

OTHER PUBLICATIONS

The Pentacam, The Gold Standard in Anterior Segment Tomography: The measurement principle. URL.: http://www.pentacam.com/sites/messprinzip.php, Archiviert in http://www.archive.org.am.09.08.2011 [abgerufen am Mar. 17, 2016], 2011.

Office Action issued in corresponding German application No. 11 2013 006 234.8 mailed Mar. 22, 2016 (w/English translation).

* cited by examiner

OPHTHALMOLOGIC APPARATUS

TECHNICAL FIELD

The present invention relates to an ophthalmologic apparatus that optically examines an eye.

BACKGROUND TECHNOLOGY

Types of ophthalmologic apparatuses include ophthalmologic imaging apparatuses for obtaining images of an eye and ophthalmologic measuring apparatuses for measuring characteristics of an eye.

Examples of ophthalmologic imaging apparatuses include an optical coherence tomography (OCT) apparatus that obtains tomographic images using OCT, a fundus camera that photographs a fundus, a scanning laser ophthalmoscope (SLO) that obtains images of a fundus by laser scanning with a confocal optical system, a slit lamp that obtains images by photographing an optical section of a cornea using slit light, and the like.

Examples of ophthalmologic measuring apparatuses include an eye refractivity examination apparatus (refractometer, keratometer) that measures refractive properties of an eye, a tonometer, a specular microscope that obtains properties of a cornea (cornea thickness, cellular distribution, etc.), a wave-front analyzer that obtains aberration information of an eye using a Shack-Hartmann sensor, and the like.

Regarding ophthalmic examinations using these apparatuses, in terms of precision and accuracy of examinations, position adjustment between the optical system of the apparatus and an eye is very important. Such position adjustment includes alignment and tracking. Alignment includes the action of aligning the light axis of the optical system of the apparatus with respect to the axis of an eye (xy alignment), as well as the action of adjusting the distance between the eye and the optical system of the apparatus (z alignment). Tracking is a function of detecting the movement of an eye and causing the position of the optical system of the apparatus to follow the eye movement.

[Patent Document 1] Japanese Unexamined Patent Application Publication No. 2009-112664

[Patent Document 2] Japanese Patent No. 4136690

SUMMARY OF THE INVENTION

Problems to be Solved by the Invention

In the conventional technologies, position adjustment in the xy direction (direction perpendicular to the optical axis) and position adjustment in the z direction (direction along the optical axis) are performed in different manners. That is, as it is necessary for position adjustment to detect the positional relationship between the optical system of the apparatus and the eye, the positional relationship in the xy direction and that in the z direction are obtained in different manners. This causes a difference between the both position adjustments, resulting in such problems as the reduced accuracy of captured images and measured values, a reduction in the reproducibility of examination, and the like.

In particular, in the conventional technologies, it is difficult to perform high-precision position adjustment in the z direction with high accuracy, and an additional device such as a dedicated sensor is required to suitably perform the position adjustment.

An objective of the present invention is to provide an ophthalmologic apparatus that is capable of performing suitable position adjustment between an optical system of the apparatus and a subject's eye.

Means of Solving the Problems

An ophthalmologic apparatus of an embodiment includes an examination optical system configured to be used to examine an eye; a drive part configured to move the examination optical system; two or more imaging parts configured to substantially simultaneously photograph an anterior segment of the eye from different directions; an analyzer configured to analyze two or more photographic images captured substantially simultaneously by the two or more imaging parts to obtain a three-dimensional position of the eye; a storage configured to store correction information, acquired in advance based on optical properties of an eyeball, for a position of an eye in an optical axis direction of the examination optical system; a position corrector configured to correct the three-dimensional position obtained by the analyzer based on the correction information; and a controller configured to control the drive part based on the three-dimensional position corrected to move the examination optical system.

Effects of the Invention

According to the present invention, it is possible to suitably perform position adjustment between an optical system of the apparatus and a subject's eye.

MODE FOR CARRYING OUT THE INVENTION

Embodiments of ophthalmologic apparatuses related to the present invention are explained in detail with reference to the accompanying drawings. Ophthalmologic apparatuses related to the present invention are used for optical examinations of the eye. Such ophthalmologic apparatuses include ophthalmologic imaging apparatuses and ophthalmologic measuring apparatuses as mentioned above. Examples of ophthalmologic imaging apparatuses include an OCT apparatus, a fundus camera, a scanning laser ophthalmoscope, a slit lamp microscope, and the like. Examples of ophthalmologic measuring apparatuses include an eye refractivity examination apparatus, a tonometer, a specular microscope, a wave-front analyzer, and the like. Cases of applying the present invention to an OCT apparatus are explained in the following embodiments; however, the present invention may be applied to any other types of ophthalmologic apparatuses.

In this specification, images obtained by OCT are sometimes referred to as OCT images. Further, a measuring action for forming an OCT image is sometimes referred to as an OCT measurement. Note that the contents of the documents cited in this specification may be employed in the following embodiments.

In the following embodiments, an OCT apparatus using OCT of so-called spectral domain type, in which a low-coherence light source and a spectrometer are included, is described; however, the present invention may also be applied to OCT apparatuses using other types than spectral domain, such as swept source type and enface type. Note that the swept source OCT is a modality of imaging the morphology of an object by: scanning (sweeping) the wavelength of light that is irradiated to the object; acquiring the spectral intensity distribution by successively detecting interference light obtained from superposing the reflected light of the light of each wavelength on reference light; and performing Fourier transform on the acquired spectral intensity distribution. The enface OCT is a modality of irradiating light with a predetermined beam diameter to an object and analyzing the components of interference light obtained from superposing the reflected light thereof on reference light, thereby forming an image of a cross-section of the object perpendicular to the travelling direction of the light, and it is also referred to as full field type.

An apparatus that is configured by combining an OCT apparatus and a fundus camera is explained in the following embodiment; however, the scope in which the present invention is applicable is not limited to such combination apparatuses. The present invention may be applied to an ophthalmologic apparatus with a single function (e.g., a fundus camera).

[Configuration]

Figure 1:
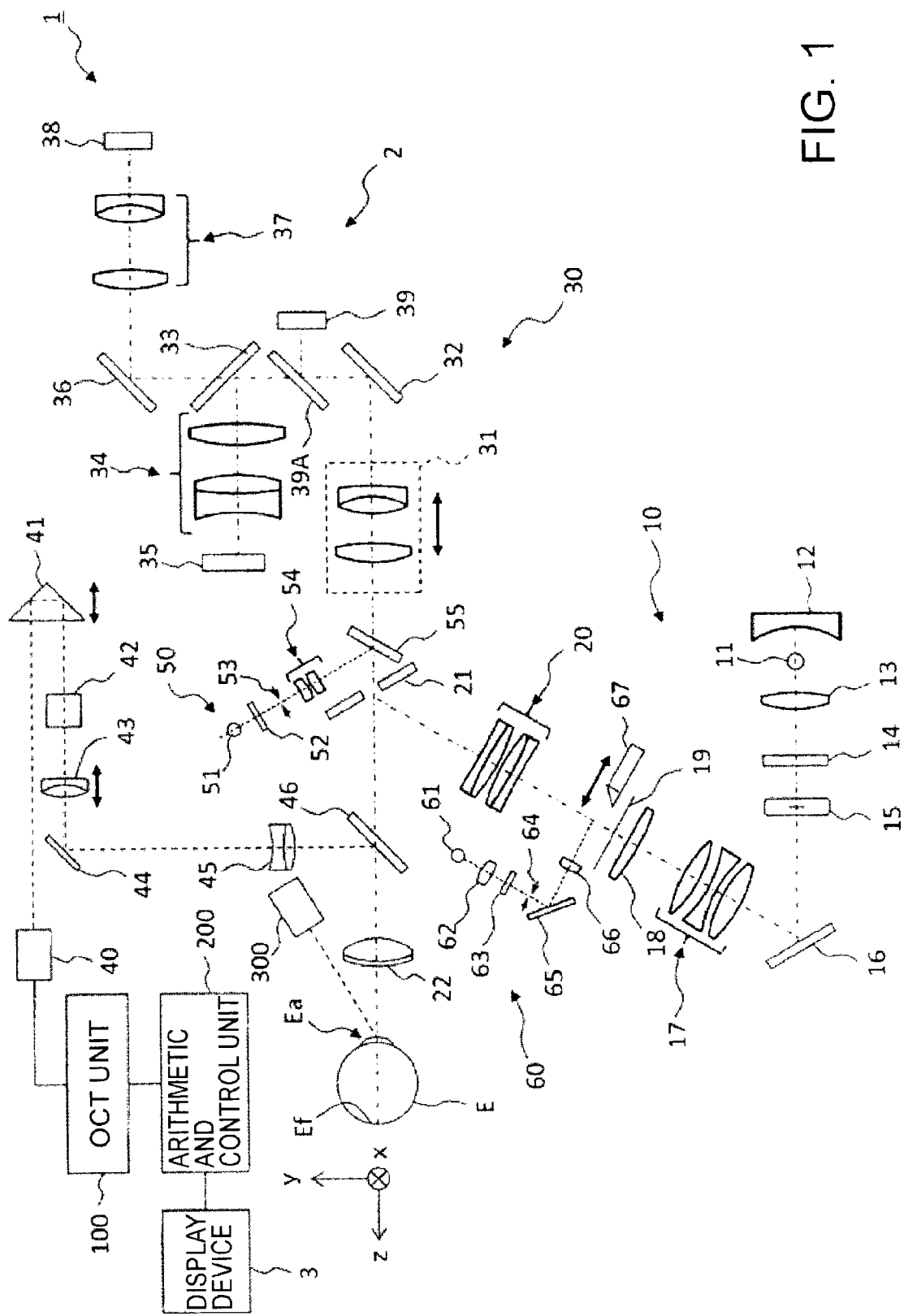
FIG. 1 is a schematic diagram illustrating an example of a configuration of an ophthalmologic apparatus according to an embodiment.

As illustrated in FIG. 1, an ophthalmologic apparatus 1 includes a fundus camera unit 2, an OCT unit 100, and an arithmetic and control unit 200. The fundus camera unit 2 has almost the same optical system as a conventional fundus camera. The OCT unit 100 is provided with an optical system for obtaining an OCT image of a fundus. The arithmetic and control unit 200 is provided with a computer that performs various arithmetic processes, control processes, and the like.

[Fundus Camera Unit]

The fundus camera unit 2 illustrated in FIG. 1 is provided with an optical system for forming a two-dimensional image (fundus image) representing the surface morphology of the fundus Ef of the eye E. Fundus images include observation images, photographic images, and the like. The observation image is, for example, a monochrome moving image formed at a prescribed frame rate using near-infrared light. Note that when the optical system is focused on the anterior eye segment Ea of the eye E, the fundus camera unit 2 may obtain an observation image of the anterior eye segment Ea. The photographic image is, for example, a color image captured by flashing visible light or a monochrome still image using near-infrared light or visible light as illumination light. The fundus camera unit 2 may be configured to be capable of acquiring other types of images such as a fluorescein angiography image, an indocyanine green fluorescent image, and a fundus autofluorescent image.

The fundus camera unit 2 is provided with a jaw holder and a forehead rest for supporting the face of the subject. The jaw holder and the forehead rest correspond to a supporter 440 illustrated in FIGS. 4A and 4B. Note that, in FIGS. 4A and 4B, reference numeral 410 indicates a base that accommodates arithmetic and control circuits and a drive system such as an optical system driver 2A and the like. Reference numeral 420 indicates a case that is located on the base 410 and accommodates optical systems. Reference numeral 430 indicates a lens case that protrudes from the front surface of the case 420 and accommodates an objective lens 22.

The fundus camera unit 2 is provided with an illumination optical system 10 and an imaging optical system 30. The illumination optical system 10 irradiates illumination light to the fundus Ef. The imaging optical system 30 guides the illumination light reflected from the fundus to imaging devices (CCD image sensors 35 and 38, sometimes simply referred to as "CCD"). Moreover, the imaging optical system 30 guides signal light coming from the OCT unit 100 to the fundus Ef, and guides the signal light having passed through the fundus Ef to the OCT unit 100.

An observation light source 11 of the illumination optical system 10 includes, for example, a halogen lamp. The light (observation illumination light) output from the observation light source 11 is reflected by a reflection mirror 12 having a curved reflective surface, and becomes near-infrared after passing through a visible cut filter 14 via a condenser lens 13. Further, the observation illumination light is once converged near an imaging light source 15, reflected by a mirror 16, and passes through relay lenses 17 and 18, an diaphragm 19, and a relay lens 20. Then, the observation illumination light is reflected on the peripheral part (the surrounding region of an aperture part) of an aperture mirror 21, penetrates a dichroic mirror 46, and refracted by the objective lens 22, thereby illuminating the fundus Ef. Note that a light emitting diode (LED) may be used as the observation light source.

The observation illumination light reflected from the fundus is refracted by the objective lens 22, penetrates the dichroic mirror 46, passes through the aperture part formed in the center region of the aperture mirror 21, passes through a dichroic mirror 55, travels through a focusing lens 31, and is reflected by a mirror 32. Further, the fundus reflection light passes through a half mirror 39A, is reflected by a dichroic mirror 33, and forms an image on the light receiving surface of the CCD image sensor 35 by a condenser lens 34. The CCD image sensor 35 detects the fundus reflection light, for example, at a preset frame rate. An image (observation image) based on the fundus reflection light detected by the CCD image sensor 35 is displayed on a display device 3. Note that when the imaging optical system 30 is focused on the anterior eye segment, an observation image of the anterior eye segment Ea of the eye E is displayed.

The imaging light source 15 is configured, for example, by a xenon lamp. The light (imaging illumination light) output from the imaging light source 15 is irradiated to the fundus Ef via a route as with the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. An image (photographic image) based on the fundus reflection light detected by the CCD image sensor 38 is displayed on the display device 3. Note that the same device or different devices may be used as the display device 3 for displaying an observation image and the display device 3 for displaying a photographic image. Further, when similar photographing is performed by illuminating the eye E with infrared light, an infrared photographic image is displayed. Moreover, an LED may be used as the imaging light source.

A liquid crystal display (LCD) 39 displays a fixation target, a visual target for measuring visual acuity, etc. The fixation target is a visual target for fixating the eye E, and is used during fundus photography and OCT measurement.

Part of the light output from the LCD 39 is reflected by the half mirror 39A, reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef.

By changing a display position of the fixation target on the screen of the LCD 39, a fixation position of the eye E can be changed. Examples of the fixation position of the eye E include, as in conventional fundus cameras, for example, a position for acquiring an image centered on the macula of the fundus Ef, a position for acquiring an image centered on the optic disc, a position for acquiring an image centered on the fundus center between the macula and the optic disc, and the like. Moreover, the display position of the fixation target may be arbitrarily changed.

Further, as with conventional fundus cameras, the fundus camera unit 2 is provided with an alignment optical system 50 and a focus optical system 60. The alignment optical system 50 generates a target (alignment indicator) for position adjustment of the optical system with respect to the eye E (alignment). A configuration for projecting the alignment indicator onto the eye E corresponds to an example of a "projection optical system". The focus optical system 60 generates a target (split target) for adjusting the focus with respect to the eye E.

The light (alignment light) output from the LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the eye E by the objective lens 22.

The alignment light reflected from the cornea travels through the objective lens 22, the dichroic mirror 46 and the abovementioned aperture part, and part of the cornea reflection light penetrates the dichroic mirror 55, passes through the focusing lens 31, is reflected by the mirror 32, penetrates the half mirror 39A, is reflected by the dichroic mirror 33, and is projected onto the light receiving surface of the CCD image sensor 35 by the condenser lens 34. An image (alignment indicator) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator to move the optical system (automatic alignment). Note that, in the embodiment, automatic alignment can be performed using anterior eye cameras 300 (described later); therefore, the ability of automatic alignment using the alignment indicator is not necessarily required. However, when automatic alignment using the anterior eye cameras 300 fails, automatic alignment may be performed using an alignment indicator, or automatic alignment using the anterior eye cameras 300 and automatic alignment using the alignment indicator may be selectively used.

To conduct focus adjustment, the reflective surface of a reflection rod 67 is placed aslant in the optical path of the illumination optical system 10. The light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus passes through the same route as the cornea reflection light of the alignment light and is detected by the CCD image sensor 35. An image (split target) captured by the CCD image sensor 35 is displayed on the display device 3 together with an observation image. As in the conventional case, the arithmetic and control unit 200 analyzes the position of the split target, and moves the focusing lens 31 and the focus optical system 60 for focusing (automatic focusing). The user may perform the focusing manually while visually checking the split target.

The dichroic mirror 46 branches the optical path for OCT measurement from the optical path for fundus photography. The dichroic mirror 46 reflects light of wavelengths used in OCT measurement and transmits light for fundus photography. This optical path for OCT measurement is provided with, in order from the OCT unit 100 side, a collimator lens unit 40, an optical path length changing part 41, a galvano scanner 42, a focusing lens 43, a mirror 44, and a relay lens 45.

The optical path length changing part 41 is movable in the direction indicated by the arrow in FIG. 1, thereby changing the length of the optical path for OCT measurement. This change of the optical path length is used for correcting the optical path length according to the axial length of the eye E, adjusting the interference state, and the like. The optical path length changing part 41 includes, for example, a corner cube and a mechanism for moving it.

The galvano scanner 42 changes the travelling direction of light (signal light LS) travelling through the optical path for OCT measurement. Thereby, the fundus Ef may be scanned with the signal light LS. The galvano scanner 42 includes, for example, a galvano mirror for scanning the signal light LS in the x direction, a galvano mirror for scanning in the y direction, and a mechanism for independently driving them. Accordingly, the signal light LS may be scanned in any direction on the xy plane.

Figure 4A:
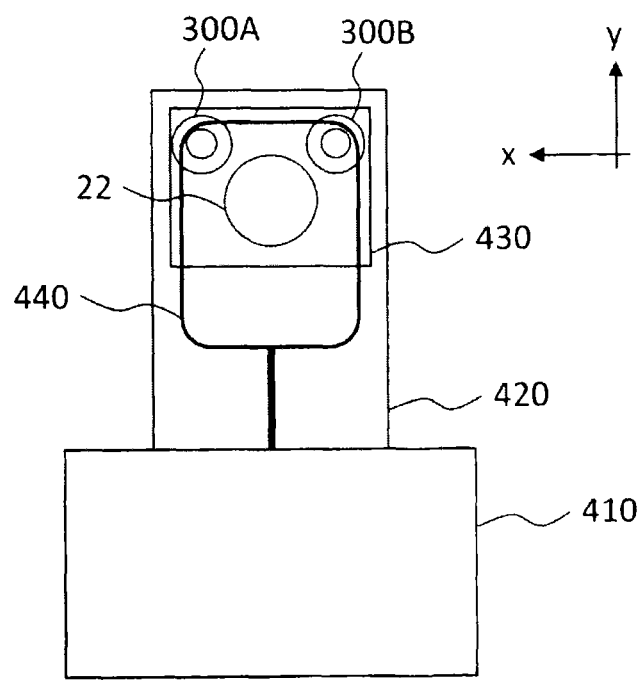
FIG. 4A is a schematic diagram illustrating an example of a configuration of an ophthalmologic apparatus according to an embodiment.
Figure 4B:
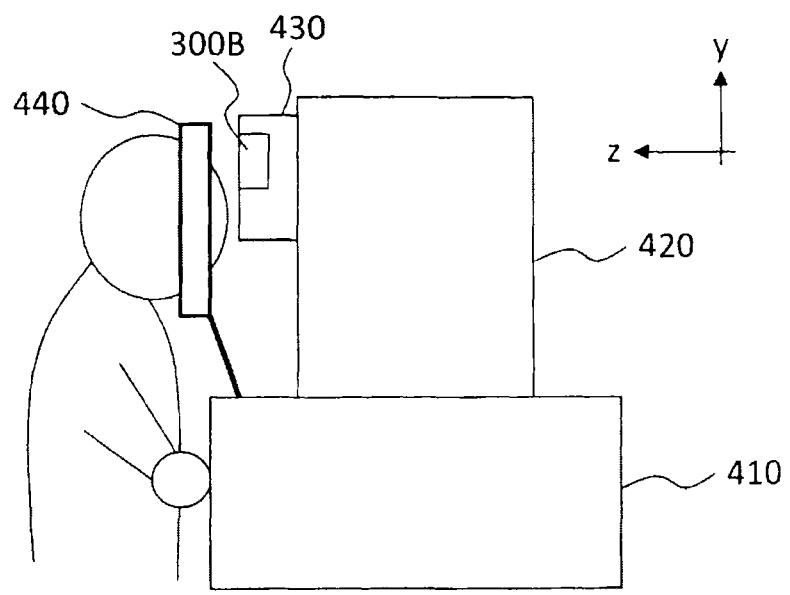
FIG. 4B is a schematic diagram illustrating an example of a configuration of an ophthalmologic apparatus according to an embodiment.

The fundus camera unit 2 is provided with the anterior eye cameras 300. The anterior eye cameras 300 substantially simultaneously photograph an anterior eye segment Ea from different directions. In the embodiment, two cameras are provided on the subject side surface of the fundus camera unit 2 (see anterior eye cameras 300A and 300B in FIG. 4A). Moreover, the anterior eye cameras 300A and 300B are, as illustrated in FIGS. 1 and 4A, arranged in positions away from the optical path of the illumination optical system 10 and the optical path of the imaging optical system 30. The two anterior eye cameras 300A and 300B may be collectively represented by the reference numeral 300.

In the embodiment, while the two anterior eye cameras 300A and 300B are provided, the number of anterior eye cameras may be any number more than one. However, taking into consideration the arithmetic process (described later), it is only required to be capable of substantially simultaneously photographing the anterior eye segment from two different directions. Moreover, in the embodiment, the anterior eye cameras 300 are separately provided from the illumination optical system 10 and the imaging optical system 30; however, similar anterior-eye photography may be performed using at least the imaging optical system 30. That is, one of the two or more anterior eye cameras may include the imaging optical system 30. In any case, in the embodiment, the anterior eye segment may be substantially simultaneously photographed from two (or more) different directions.

Note that "substantially simultaneously" indicates to allow photographing timing deviation of such a degree that eye movement can be ignored in photography using two or more anterior eye cameras. Accordingly, images of the eye E located in substantially the same position (orientation) may be acquired by the two or more anterior eye cameras.

Moreover, photography with the two or more anterior eye cameras may be moving image photography or still image photography; however, in the embodiment, moving image photography is described in detail. In the case of moving image photography, substantially simultaneous photography of the anterior eye segment mentioned above may be realized by controlling the timing to start photography, or controlling frame rates and/or the timing to capture frames. Meanwhile, in the case of still image photography, this may be realized by controlling the timing for photography.

[OCT Unit]

Figure 2:
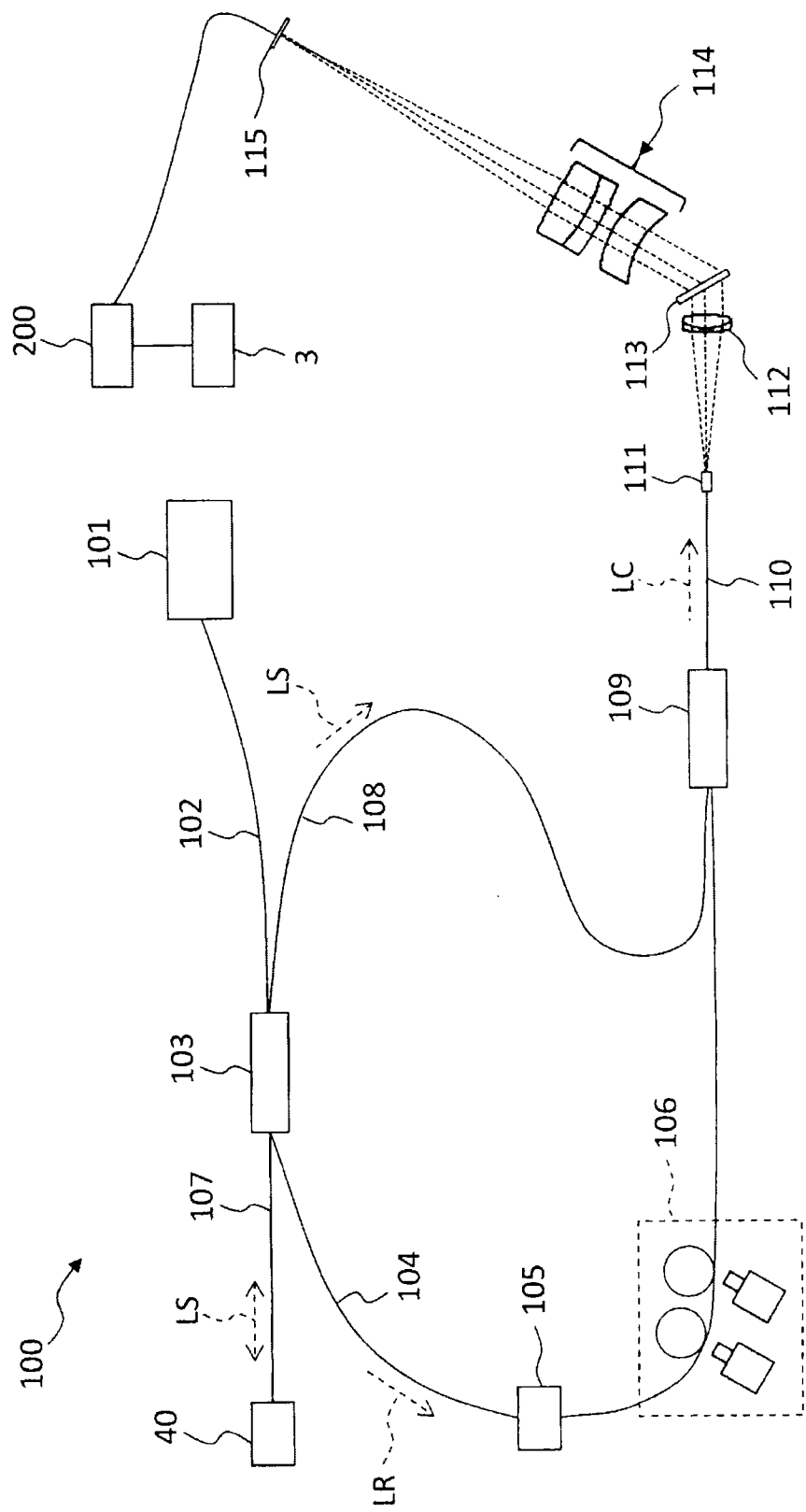
FIG. 2 is a schematic diagram illustrating an example of a configuration of an ophthalmologic apparatus according to an embodiment.

An example of the configuration of the OCT unit 100 is described with reference to FIG. 2. The OCT unit 100 is provided with an optical system for acquiring an OCT image of the fundus Ef. The optical system has a similar configuration to a conventional spectral domain OCT. That is, the optical system is configured to split low-coherence light into reference light and signal light, make the signal light having propagated through a fundus and the reference light having passed through a reference optical path interfere with each other to generate interference light, and detect the spectral components of this interference light. The detection result (detection signal) is sent to the arithmetic and control unit 200.

Note that, in the case of swept source OCT, a wavelength tunable light source is provided instead of a light source that outputs low-coherence light, while an optical element for spectrally decomposing interference light is not provided. Generally, regarding the configuration of the OCT unit 100, known technologies may be applied according to the type of OCT.

A light source unit 101 outputs broadband low-coherence light L0. The low-coherence light L0 includes, for example, near-infrared wavelengths (approximately 800 nm to 900 nm), and has a temporal coherence length of around several tens of micrometers. Note that wavelengths not visible to the human eye, such as near-infrared light with a central wavelength of around 1040 nm to 1060 nm, may be used as the low-coherence light L0.

The light source unit 101 includes a light output device, such as a super luminescent diode (SLD), an LED, a semiconductor optical amplifier (SOA), or the like.

The low coherence light L0 output from the light source unit 101 is guided to a fiber coupler 103 by an optical fiber 102 and split into signal light LS and reference light LR.

The reference light LR is guided by an optical fiber 104 and arrives at an optical attenuator 105. The optical attenuator 105 automatically adjusts the amount of the reference light LR guided by the optical fiber 104 under the control of the arithmetic and control unit 200 using a known technology. The reference light LR whose amount have been adjusted by the optical attenuator 105 is guided by the optical fiber 104 and arrives at a polarization adjuster (polarization controller) 106. The polarization adjuster 106 is a device that, by applying external stress to the looped optical fiber 104, adjusts the polarization condition of the reference light LR guided in the optical fiber 104. Note that the configuration of the polarization adjuster 106 is not limited to this and any known technologies may be used. The reference light LR whose polarization condition has been adjusted by the polarization adjuster 106 arrives at a fiber coupler 109.

The signal light LS generated by the fiber coupler 103 is guided by an optical fiber 107 and collimated into a parallel light flux by the collimator lens unit 40. Further, the signal light LS arrives at the dichroic mirror 46 via the optical path length changing part 41, the galvano scanner 42, the focusing lens 43, the mirror 44, and the relay lens 45. Subsequently, the signal light LS is reflected by the dichroic mirror 46, refracted by the objective lens 22, and projected onto the fundus Ef. The signal light LS is scattered (including reflections) at various depth positions of the fundus Ef. Back-scattered light of the signal light LS from the fundus Ef reversely advances along the same route as the outward path and is guided by the fiber coupler 103, thereby arriving at the fiber coupler 109 via an optical fiber 108.

The fiber coupler 109 causes the back-scattered light of the signal light LS and the reference light LR having passed through the optical fiber 104 to interfere with each other. Interference light LC thus generated is guided by an optical fiber 110 and output from an exit end 111. Further, the interference light LC is converted to a parallel light flux by a collimator lens 112, spectrally divided (spectrally decomposed) by a diffraction grating 113, converged by a convergence lens 114, and projected onto the light receiving surface of a CCD image sensor 115. Note that although the diffraction grating 113 illustrated in FIG. 2 is of transmission type, it is possible to use a spectrally decomposing element of any other type, such as a diffraction grating of reflection type.

The CCD image sensor 115 is, for example, a line sensor, and detects the spectral components of the spectrally decomposed interference light LC and converts the components into electric charges. The CCD image sensor 115 accumulates the electric charges to generate a detection signal, and sends the signal to the arithmetic and control unit 200.

Although a Michelson interferometer is employed in this embodiment, it is possible to employ any type of interferometer such as a Mach-Zehnder-type as appropriate. Instead of a CCD image sensor, other types of image sensor, such as a complementary metal-oxide semiconductor (CMOS) image sensor, may be used.

[Arithmetic and Control Unit]

The configuration of the arithmetic and control unit 200 is described. The arithmetic and control unit 200 analyzes the detection signal fed from the CCD image sensor 115 to form an OCT image of the fundus Ef. An arithmetic process for this is the same as that of a conventional spectral domain OCT.

Further, the arithmetic and control unit 200 controls each part of the fundus camera unit 2, the display device 3, and the OCT unit 100. For example, the arithmetic and control unit 200 displays an OCT image of the fundus Ef on the display device 3.

Moreover, as control of the fundus camera unit 2, the arithmetic and control unit 200 performs: control of action of the observation light source 11, the imaging light source 15 and the LEDs 51 and 61; control of action of the LCD 39; control of movement of the focusing lenses 31 and 43; control of movement of the reflection rod 67; control of movement of the focus optical system 60; control of movement of the optical path length changing part 41; control of action of the galvano scanner 42; control of action of the anterior eye cameras 300; and the like.

Further, as control of the OCT unit 100, the arithmetic and control unit 200 performs: control of action of the light source unit 101; control of action of the optical attenuator 105; control of action of the polarization adjuster 106; control of action of the CCD image sensor 115; and the like.

The arithmetic and control unit 200 includes, for example, a microprocessor, RAM, ROM, a hard disk drive, a communication interface, and the like, as in conventional computers. The storage device such as a hard disk drive stores computer programs for controlling the ophthalmologic apparatus 1. The arithmetic and control unit 200 may be provided with various types of circuit boards, such as a circuit board for forming OCT images. The arithmetic and control unit 200 may further include an operation device (input device) such as a keyboard and a mouse, and a display device such as LCD.

The fundus camera unit 2, the display device 3, the OCT unit 100, and the arithmetic and control unit 200 may be integrally provided (i.e., in a single case), or they may be distributed to two or more cases.

[Control System]

Figure 3:
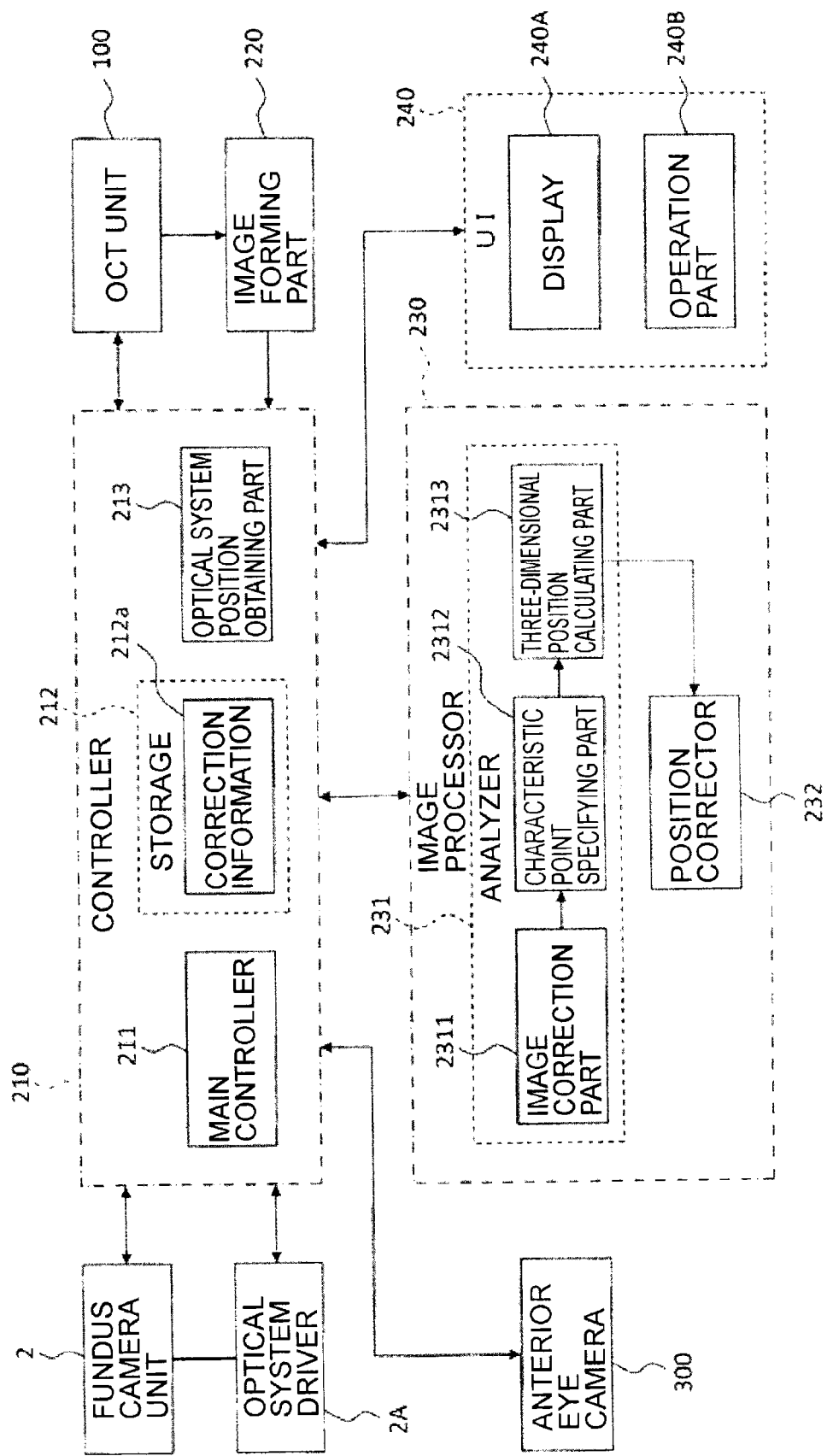
FIG. 3 is a schematic block diagram illustrating an example of a configuration of an ophthalmologic apparatus according to an embodiment.

The configuration of a control system of the ophthalmologic apparatus 1 is described with reference to FIG. 3.

(Controller)

The control system of the ophthalmologic apparatus 1 is configured with a controller 210 as a center. The controller 210 includes, for example, the aforementioned microprocessor, RAM, ROM, a hard disk drive, and a communication interface, etc. The controller 210 is provided with a main controller 211, a storage 212, and an optical system position obtaining part 213.

(Main Controller)

The main controller 211 performs various types of controls mentioned above. Note that the movement control of the focusing lens 31 is to control a focus driver (not illustrated) to move the focusing lens 31 in the optical axis direction. This changes the focusing position of the imaging optical system 30. The main controller 211 is capable of controlling the optical system driver 2A to three-dimensionally move the optical system installed in the fundus camera unit 2.

This control is implemented by automatic alignment and/or tracking. Here, tracking is to move the optical system of the apparatus according to the eye movement of the eye E. Tracking is performed at, for example, the stage after alignment (focusing is also performed in advance in some cases). Tracking is a function of maintaining a suitable positional relationship in which alignment (and focus) is matched by causing the position of the optical system of the apparatus to follow the eye movement.

Note that the optical system driver 2A of the embodiment moves the optical system installed in the fundus camera unit 2; however, the optical system driver 2A may be configured to move the optical system installed in the OCT unit 100 as well as the optical system installed in the fundus camera unit 2. The optical system driver 2A is an example of "drive part".

The anterior eye cameras 300 of the embodiment are provided on the case of the fundus camera unit 2, and therefore can be moved by controlling the optical system driver 2A. Moreover, it is possible to provide a photography moving part that is capable of independently moving the two or more anterior eye cameras 300. Specifically, the photography moving part may include a driving mechanism (actuator, power transmission mechanism, etc.) provided with respect to each of the anterior eye cameras 300. The photography moving part may also be configured to move the two or more anterior eye cameras 300 by transmitting power generated by a single actuator through a power transmission mechanism of each of the anterior eye cameras 300.

The main controller 211 performs a process of writing data into the storage 212, and a process of reading out data from the storage 212.

(Storage)

The storage 212 stores various types of data. Examples of the data stored in the storage 212 include, for example, image data of an OCT image, image data of a fundus image, and eye information. The eye information includes information related to a subject such as patient ID and name, information related to the subject's eye such as identification information of left eye/right eye, and the like. The storage 212 further stores various types of programs and data to run the ophthalmologic apparatus 1.

The storage 212 stores correction information 212a in advance. The correction information 212a is information acquired based on optical properties of eyeballs, and is used to correct the position of the eye in the optical axis direction of the examination optical system. The examination optical system is an optical system used for examinations (photography of eyes, OCT measurements, etc.) performed by the ophthalmologic apparatus 1. In this embodiment, the optical systems provided in the fundus camera unit 2 and the OCT unit 100 correspond to the examination optical system. Besides, in this embodiment, the optical axis of the examination optical system corresponds to the optical axis of the imaging optical system 30. The optical axis of the imaging optical system 30 is common to the optical axis of the illumination optical system 10 and that of the optical system for OCT measurements.

As described in detail below, the ophthalmologic apparatus 1 photographs the anterior eye segment Ea substantially simultaneously from different directions, and analyzes two photographic images captured thereby to obtain the three-dimensional position of the eye E. The correction information 212a is used for correction of the three-dimensional position.

Figure 5:
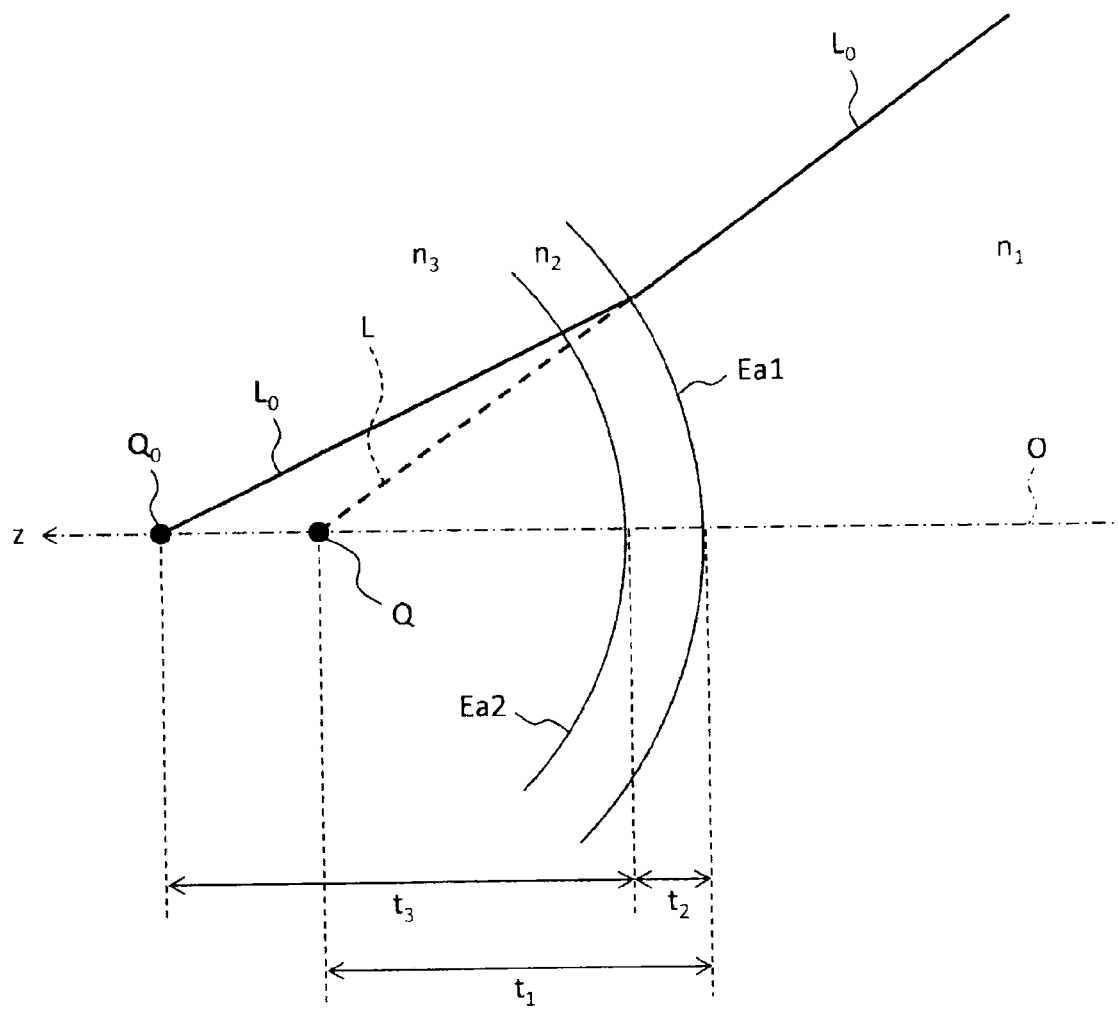
FIG. 5 is a schematic diagram for explaining correction information of an ophthalmologic apparatus according to an embodiment.

With reference to FIG. 5, a description is given of an example of the correction information 212a. In this embodiment, images of the anterior eye segment Ea of the eye E are captured by the anterior eye cameras 300A and 300B, and the photographic images captured are analyzed to obtain the three-dimensional position of the eye E. In this analysis, the three-dimensional position of a characteristic point of the anterior eye segment Ea is obtained. The cornea is unsuitable as the characteristic point because it is transparent. Therefore, a dark part of the eye (the pupil, the iris) is set as the characteristic point. However, since the pupil and the iris are intraocular tissues, the position of the characteristic point obtained from the photographic images varies depending on the refractive power of the anterior eye segment. The refractive power of the anterior eye segment causes the displacement of the characteristic point especially in the optical axis direction of the examination optical system. This displacement corresponds to the difference between position Q and position $Q_0$ illustrated in FIG. 5.

Reference sign O indicates the optical axis of the examination optical system (the imaging optical system 30 etc.). Although not illustrated, the examination optical system is arranged on the right side of FIG. 5. Reference sign Ea1 represents the front face of the cornea Ea (anterior corneal surface), while reference sign Ea2 represents the rear face of the cornea Ea (posterior corneal surface). The curvature radius of the anterior corneal surface Ea1 is indicated by $r_1$, and that of the posterior corneal surface Ea2 by $r_2$. The characteristic point is the center of the pupil, i.e., the center (apex)

of the front face of the crystalline lens. Reference sign $Q_0$ indicates the actual position of the pupil center, while reference sign Q indicates the apparent position of the pupil center. Reference sign $n_1$ represents the refractive index of the air, reference sign $n_2$ represents the refractive index of the cornea, and the reference sign $n_3$ represents the refractive index of the anterior chamber (aqueous humor). The distance between the anterior corneal surface Ea1 and the apparent position Q of the pupil center is represented by $t_1$. The thickness of the cornea Ea is represented by $t_2$. The distance between the posterior corneal surface Ea2 and the actual position $Q_0$ of the pupil center is represented by $t_3$.

Light L incident on the anterior eye cameras 300 from the actual position $Q_0$ of the pupil center is refracted at the anterior eye segment (cornea Ea, aqueous humor). When viewed from the side of the anterior eye cameras 300, the light L appears to have traveled through the path $L_0$ indicated by a broken line. Accordingly, the pupil center present in the actual position $Q_0$ is recognized as being located in the apparent position Q in photographic images.

The distance WD from the apex (surface apex) of the front face of the objective lens 22 to the apparent position Q of the pupil center can be expressed as follows: $WD=WD_0+t_1$, where $WD_0$ represents a general working distance that indicates the distance from the apex of the objective lens 22 to the anterior corneal surface. The general working distance $WD_0$ is set to, for example, 34.8 mm. It is necessary to calculate the distance $t_1$ to obtain the distance WD. Described below is an example of the calculation of the distance $t_1$. For simplicity of explanation, an example of paraxial approximation calculation is explained.

Assuming that the refractive power of the anterior corneal surface Ea1 is $D_1$, the refractive power of the posterior corneal surface Ea2 is $D_2$, and the refractive power of the cornea Ea is $D_3$, the relationship among these powers is represented as follows:

$$D_1=n_2/f_1=(n_2-n_1)/r_1$$

$$D_2=n_3/f_2=(n_3-n_2)/r_2$$

$$D_3=n_3/f_3=D_1+D_2-(t_2/n_2)D_1D_2$$

where the focal length of the anterior corneal surface Ea1 is $f_1$, the focal length of the posterior corneal surface Ea2 is $f_2$, and the focal length of the cornea Ea is $f_3$.

When it is assumed that the principal plane positions of the cornea Ea on the object side and the image side coincide with the anterior corneal surface Ea1, the following relationship is obtained:

$$(n_1/t_1)=(n_3/f_3)-[n_3/(t_2+t_3)] \qquad (1)$$

The distance $t_1$ can be calculated from this relational expression. Note that the principal plane position may be calculated for each of the object side and the image side for the above calculation (see modification described below).

To calculate the distance $t_1$ from equation (1), it is necessary to obtain the values of parameters $n_1$, $n_3$, $f_3$, $t_2$, and $t_3$. As the values of these parameters, for example, the values of a model eye are employed. The model eye can be of any type (Gullstrand model eye, Navarro model eye, Le Grand model eye, etc.).

In the case of the Gullstrand model eye, the following values are used:
the refractive index $n_1$ of the air=1;
the refractive index $n_3$ of the aqueous humor=1.336;
the focal length $f_3$ of the cornea Ea=31.03 mm;
the thickness $t_2$ of the cornea Ea=0.5 mm;
the distance $t_3$ between the posterior corneal surface Ea2 and the actual position $Q_0$ of the pupil center=3.1 mm.

With these values, it is obtained that the distance $t_1$=3.05 mm. Thus, the distance $WD=WD_0+3.05=37.85$ mm from the apex of the objective lens 22 to the apparent position Q of the pupil center is obtained. Incidentally, it is possible to reflect the refractive index of the cornea. For example, in the Gullstrand eye model, a refractive index of 1.376 may be used for the anterior corneal surface Ea1, and a refractive index of 1.336 for the posterior corneal surface Ea2.

While the above example is described of paraxial approximation calculation, the distance $t_1$ and the distance WD may be calculated by simulation (actual ray tracing, etc.).

Although the values of the model eye are used in the above example, a measured value of the eye E may be used for any of the parameters. For example, an OCT image of the anterior eye segment Ea may be analyzed to obtain the thickness of the cornea Ea (distance $t_2$), the depth of the aqueous humor (distance $t_3$), the distance between the anterior corneal surface Ea1 and the front of the crystalline lens (distance $t_2+t_3$), the curvature radius $r_1$ of the anterior corneal surface Ea1, the curvature radius $r_2$ of the posterior corneal surface Ea2, and the like to use them. The refractive power and the curvature radius of the cornea Ea obtained by a refractometer or a keratometer may also be used. The measured values are obtained in advance and stored in the storage 212. Such pre-measurement may be performed by the ophthalmologic apparatus 1, or it may be performed by another ophthalmologic apparatus. Since the refractive power of the anterior corneal surface Ea1 is dominant in the refractive power of the anterior eye segment Ea, the same operation as above may be performed based on the curvature radius $r_1$ of the anterior corneal surface Ea1.

For example, if values indicated by the model eye are used for all the above parameters, the correction amount (displacement) of the three-dimensional position of the characteristic point of the anterior eye segment Ea can be obtained in advance, and this may be applied to an arbitrary eye. In this case, the value of the displacement may be stored as the correction information 212*a*. Accordingly, a position corrector 232 (described later) is not required to calculate the displacement. Incidentally, as is clear from FIG. 5, the displacement ($\Delta t$) can be obtained by the following equation: $\Delta t=t_2+t_3-t_1$.

On the other hand, when the displacement is calculated for each eye E, measured values of the optical properties (optical characteristic information) obtained beforehand for the anterior eye segment of the eye E are stored as the correction information 212*a*. Further, as the correction information 212*a*, standard values of the optical properties of the anterior eye segment indicated by the model eye or the like may also be stored. The position corrector 232 (described later) calculates the displacement $\Delta t$ due to the influence of the anterior eye segment Ea of the eye E based on the correction information 212*a* including the optical characteristic information and the standard values. This calculation is performed based on the above algorithm or simulation.

Although not illustrated, the storage 212 stores aberration information in advance. The aberration information includes, for each of the anterior eye cameras 300, information regarding distortion aberration occurred in a photographic image due to effects of the optical system installed therein. Here, the optical system installed in the anterior eye cameras 300 includes, for example, an optical element that causes distortion aberration of the lens or the like. The aberration information can be referred to as a parameter that quantifies the deformation of a photographic image caused by such optical elements.

An example of a method for generating the aberration information is explained. Taking into account instrumental error (difference in distortion aberration) of the anterior eye cameras 300, the following measurements are performed for each of the anterior eye cameras 300. An operator prepares a specific reference point. The reference point is a photographing target used in detecting the distortion aberration. The operator performs photography multiple times while changing the relative position between the reference point and each of the anterior eye cameras 300. With this, a plurality of photographic images of the reference point photographed from different directions is obtained. The operator analyzes the acquired photographic images using a computer to generate the aberration information of the anterior eye camera 300. Note that the computer that performs this analysis process may be an image processor 230 or any other computer (computer for inspection before shipping products, computer for maintenance, etc.).

The analysis process for generating the aberration information includes, for example, the following steps:

an extraction step for extracting an image region corresponding to the reference point in each photographic image;

a distribution state calculating step for calculating the distribution state (coordinates) of the image region corresponding to the reference point in each photographic image;

a distortion aberration calculating step for calculating a parameter indicating distortion aberration based on the obtained distribution state; and a correction factor calculating step for calculating a factor for correcting the distortion aberration based on the obtained parameter.

Note that the parameter related to the distortion aberration that the optical system gives to an image may include the principal distance, the position of a principal point (in vertical and horizontal directions), the distortion of a lens (in radiation direction and tangential direction), and the like. The aberration information is constructed as information (e.g., table information) that associates the identification information of each of the anterior eye cameras 300 and the correction factor corresponding thereto. The main controller 211 stores the aberration information generated in this manner in the storage 212. The generation of such aberration information and the aberration correction based on this are referred to as camera calibration or the like.

(Optical System Position Obtaining Part)

The optical system position obtaining part 213 obtains the current position of the examination optical system installed in the ophthalmologic apparatus 1. The examination optical system is an optical system used for optically examining the eye E. The examination optical system in the ophthalmologic apparatus 1 of the embodiment (combined machine of a fundus camera and an OCT apparatus) is an optical system for obtaining images of an eye.

The optical system position obtaining part 213 receives information representing the content of the movement control of the optical system driver 2A by the main controller 211, and obtains the current position of the examination optical system moved by the optical system driver 2A. A specific example of this process is explained. The main controller 211 controls the optical system driver 2A at a predetermined timing (upon start-up of the apparatus, upon inputting patient information, etc.) and moves the examination optical system to a predetermined initial position. Thereafter, the main controller 211 records the control content each time the optical system driver 2A is controlled. Thereby, a history of the control contents may be obtained. The optical system position obtaining part 213 refers to this history and obtains the control contents up to the present time, and determines the current position of the examination optical system based on the control contents.

Alternatively, each time controlling the optical system driver 2A, the main controller 211 may send the control content thereof to the optical system position obtaining part 213 so that the optical system position obtaining part 213 can determine the current position of the examination optical system each time it receives the control content.

For another example, the optical system position obtaining part 213 may be provided with a position sensor that detects the position of the examination optical system.

When the current position of the examination optical system is obtained by the optical system position obtaining part 213 as described above, the main controller 211 can control the optical system driver 2A to move the examination optical system based on the obtained current position and the three-dimensional position of the eye E obtained by an analyzer 231 (described later). Specifically, the main controller 211 recognizes the current position of the examination optical system from the result obtained by the optical system position obtaining part 213, and recognizes the three-dimensional position of the eye E from the analysis result of the analyzer 231. Subsequently, to bring the position of the examination optical system with respect to the three-dimensional position of the eye E in a predetermined positional relationship, the main controller 211 changes the position thereof with the current position of the examination optical system as a starting point. This predetermined positional relationship indicates that the positions in the x and y directions match each other, while the distance in the z direction is a predetermined working distance.

(Image Forming Part)

An image forming part 220 forms image data of a tomographic image of the fundus Ef based on a detection signal from the CCD image sensor 115. As with a conventional spectral domain OCT, this process includes noise removal (noise reduction), filtering, fast Fourier transform (FFT), and the like. In the case of another type of OCT apparatus, the image forming part 220 performs known processes according to the type thereof.

The image forming part 220 includes, for example, the aforementioned circuit boards. Note that "image data" and the "image" based thereon may be treated in the same way in this specification.

(Image Processor)

The image processor 230 performs various types of image processing and analysis on an image formed by the image forming part 220. For example, the image processor 230 performs various correction processes such as luminance correction and dispersion compensation of the image. Further, the image processor 230 performs various types of image processing and analysis on an image (fundus image, anterior eye image, etc.) obtained by the fundus camera unit 2.

The image processor 230 performs known image processing such as an interpolation process for interpolating pixels between tomographic images, thereby forming image data of a three-dimensional image of the fundus Ef. The image data of a three-dimensional image refers to image data in which the positions of pixels are defined by the three-dimensional coordinates. Examples of the image data of a three-dimensional image include image data composed of three-dimensional arrays of voxels. This image data is referred to as volume data, voxel data, or the like. For displaying an image based on the volume data, the image processor 230 performs a rendering process (such as volume rendering, maximum intensity projection (MIP), etc.) on the volume data to form image data of a pseudo three-dimensional image taken from a specific view direction. This pseudo three-dimensional image is displayed on a display 240A.

Further, stack data of multiple tomographic images may be formed as the image data of a three-dimensional image. The stack data is image data obtained by three-dimensionally arranging the multiple tomographic images obtained along multiple scanning lines, based on the positional relationship of the scanning lines. That is, the stack data is image data obtained by expressing the multiple tomographic images originally defined by individual two-dimensional coordinate systems by a three-dimensional coordinate system (namely, embedding the images in a three-dimensional space).

The image processor 230 is further provided with the analyzer 231 and the position corrector 232.

(Analyzer)

The analyzer 231 analyzes two or more photographic images captured substantially simultaneously by the two or more anterior eye cameras 300, thereby obtaining the three-dimensional position of the eye E. As an example of a configuration for performing this process, the analyzer 231 is provided with an image correction part 2311, a characteristic point specifying part 2312, and a three-dimensional position calculating part 2313.

(Image Correction Part)

The image correction part 2311 corrects distortion of each photographic image captured by the anterior eye cameras 300 based on the aberration information stored in the storage 212. This process may be performed by, for example, known image processing technology based on a correction factor for correcting distortion aberration. Note that, if the distortion aberration caused in a photographic image due to the optical system of the anterior eye cameras 300 is sufficiently small or the like, the aberration information and the image correction part 2311 are not necessary.

(Characteristic Point Specifying Part)

The characteristic point specifying part 2312 analyzes each photographic image (with its distortion aberration corrected by the image correction part 2311), thereby specifying an image position (referred to as "characteristic point") corresponding to a predetermined characteristic point of the anterior eye segment Ea. In the following, a case is explained in which the center of the pupil is used as the characteristic point.

First, the characteristic point specifying part 2312 specifies an image region (pupil region) corresponding to the pupil of the eye E based on the distribution of pixel values (luminance values etc.) in a photographic image. Generally, the pupil is represented with lower luminance compared to other parts, and therefore, the pupil region may be specified by searching an image region with low luminance. At this time, the pupil region may be specified by taking the shape of the pupil into consideration. That is, the pupil region may be specified by searching for a substantially circular image region with low luminance.

Next, the characteristic point specifying part 2312 specifies the center position of the specified pupil region. As mentioned above, the pupil is substantially circular. Accordingly, by specifying the contour of the pupil region and then specifying the center position of the contour (an approximate circle or an approximate ellipse of the contour), this may be used as the center of the pupil. Instead, by deriving the center of the gravity of the pupil region, this center of the gravity may be used as the center of the pupil.

Note that, even in the case of specifying a characteristic position corresponding to another characteristic point, the characteristic position may be specified based on the distribution of pixel values in a photographic image in the same manner as mentioned above.

(Three-Dimensional Position Calculating Part)

The three-dimensional position calculating part 2313 calculates the three-dimensional position of the characteristic point of the eye E based on the positions of the anterior eye cameras 300 and characteristic positions specified by the characteristic point specifying part 2312 in two or more photographic images. This process is explained with reference to FIGS. 6A and 6B.

Figure 6A:
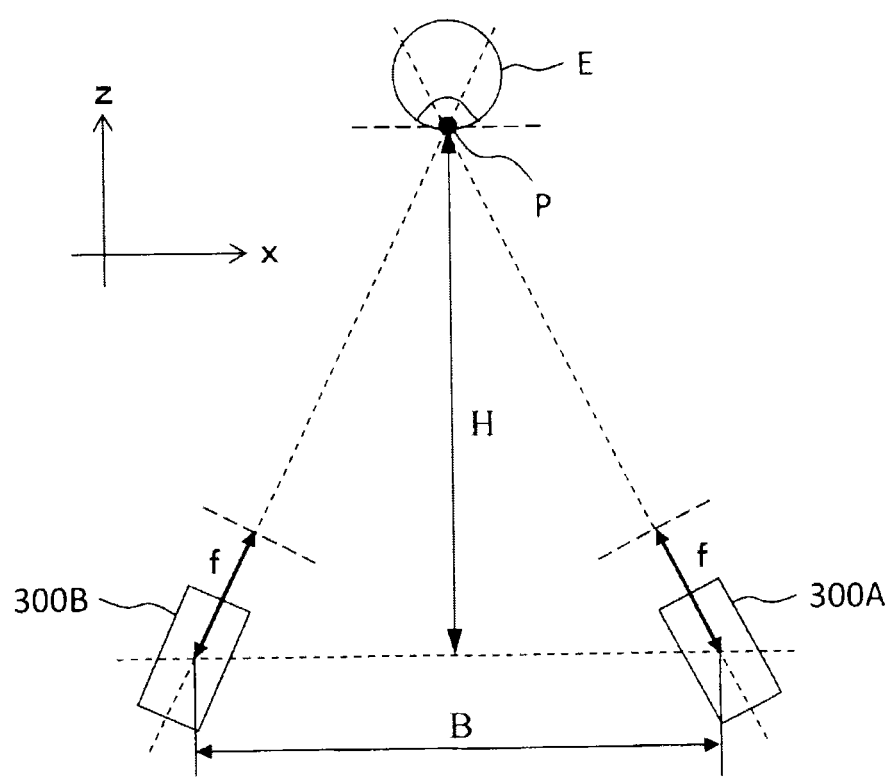
FIG. 6A is a schematic diagram for explaining processing performed by an ophthalmologic apparatus according to an embodiment.
Figure 6B:
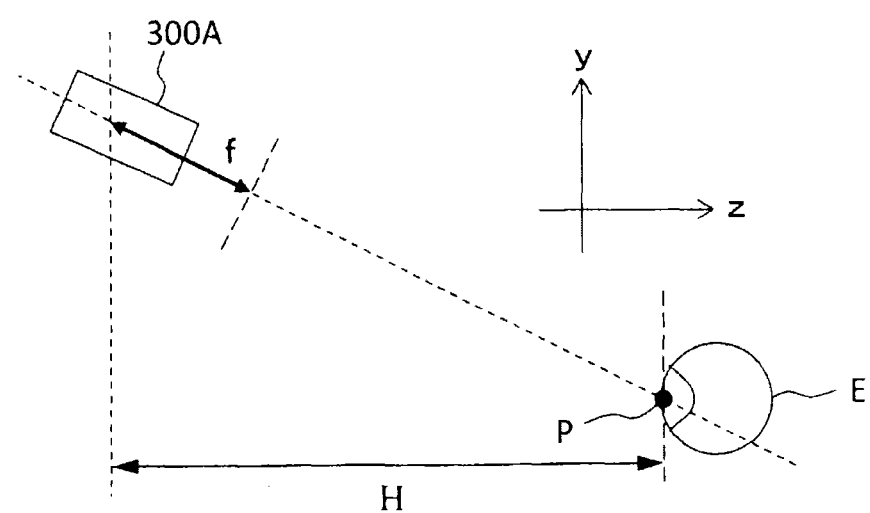
FIG. 6B is a schematic diagram for explaining processing performed by an ophthalmologic apparatus according to an embodiment.

FIG. 6A is a top view illustrating the positional relationship between the eye E and the anterior eye cameras 300A and 300B. FIG. 6B is a side view illustrating the positional relationship between the eye E and the anterior eye cameras 300A and 300B. The distance (base line length) between the two anterior eye cameras 300A and 300B is represented as "B". The distance (photographing distance) between the base line of the two anterior eye cameras 300A and 300B and a characteristic position P of the eye E is represented as "H". The distance (screen distance) between the anterior eye cameras 300A and 300B and the screen plane is represented as "f".

In such an arrangement state, the resolution of images photographed by the anterior eye cameras 300A and 300B is expressed by the following equations, where $\Delta p$ represents the pixel resolution:

$$xy \text{ resolution (planar resolution)}: \Delta xy = H \times \Delta p / f$$

$$z \text{ resolution (depth resolution)}: \Delta z = H \times H \times \Delta p / (B \times f)$$

The three-dimensional position calculating part 2313 applies known trigonometry, taking into account the positional relationship illustrated in FIGS. 6A and 6B, to the positions of the two anterior eye cameras 300A and 300B (these are known) and characteristic positions corresponding to the characteristic point P in two photographic images, thereby calculating the three-dimensional position of the characteristic point P, i.e., the three-dimensional position of the eye E.

The three-dimensional position of the eye E calculated by the three-dimensional position calculating part 2313 is sent to the controller 210. Based on this calculation result of the three-dimensional position, the controller 210 controls the optical system driver 2A such that the optical axis of the examination optical system matches the axis of the eye E, and that the distance from the examination optical system to the eye E becomes a predetermined working distance. Here, the working distance is a preset value indicating the distance between the examination optical system and the eye E during the examination using the examination optical system.

When the anterior eye cameras 300 acquire moving images of the anterior eye segment Ea in parallel from different directions, tracking of the examination optical system may be performed with respect to the movement of the eye E by performing, for example, the following processes (1) and (2):

(1) The analyzer 231 successively analyzes two or more frames captured substantially simultaneously by acquiring moving images with the two or more anterior eye cameras 300, thereby successively obtaining the three-dimensional position of the eye E.

(2) The controller 210 successively controls the optical system driver 2A based on the three-dimensional position of the eye E successively obtained by the analyzer 231, thereby causing the position of the examination optical system to follow the movement of the eye E.

(Position Corrector)

The position corrector 232 corrects the three-dimensional position of the eye E (pupil center) obtained by the three-dimensional position calculating part 2313 based on the correction information 212a stored in the storage 212. If the above displacement Δt is included in the correction information 212a, the position corrector 232 changes the three-dimensional position of the pupil center by a distance corresponding to the displacement Δt. This process is intended to move the coordinates of the three-dimensional position of the pupil center by Δt in the +z direction. That is, assuming that the coordinates of the three-dimensional position of the pupil center obtained by the three-dimensional position calculating part 2313 are represented by (x, y, z), the coordinates corrected by the position corrector 232 become (x, y, z+Δt).

If the optical characteristic information of the anterior eye segment Ea of the eye E is included in the correction information 212a, the position corrector 232 calculates the displacement Δt based on the optical characteristic information and standard values included in the correction information 212a. Further, the position corrector 232 corrects the three-dimensional position of the pupil center obtained by the three-dimensional position calculating part 2313 based on the displacements Δt thus obtained. This correction process is performed in the same manner as in the case where the displacement Δt itself is stored in the correction information 212a.

The image processor 230 that functions as described above includes, for example, the aforementioned microprocessor, RAM, ROM, a hard disk drive, a circuit board, and the like. The storage device such as a hard disk drive stores, in advance, computer programs that cause the microprocessor to implement the above functions.

(User Interface)

A user interface 240 includes the display 240A and an operation part 240B. The display 240A includes the aforementioned display device of the arithmetic and control unit 200 and the display device 3. The operation part 240B includes the aforementioned operation device of the arithmetic and control unit 200. The operation part 240B may include various types of buttons and keys provided on the case of the ophthalmologic apparatus 1 or the outside. For example, if the fundus camera unit 2 has a case similar to those of conventional fundus cameras, the operation part 240B may include a joy stick, an operation panel, and the like arranged on this case. Besides, the display 240A may include various types of display devices such as a touch panel and the like arranged on the case of the fundus camera unit 2.

Note that the display 240A and the operation part 240B need not be configured as separate devices. For example, a device like a touch panel having a display function integrated with an operation function can be used. In such cases, the operation part 240B includes this touch panel and a computer program. The content of operation via the operation part 240B is fed to the controller 210 as an electric signal. Moreover, operations and inputs of information may be performed by using a graphical user interface (GUI) displayed on the display 240A and the operation part 240B.

[Operation]

Figure 7:
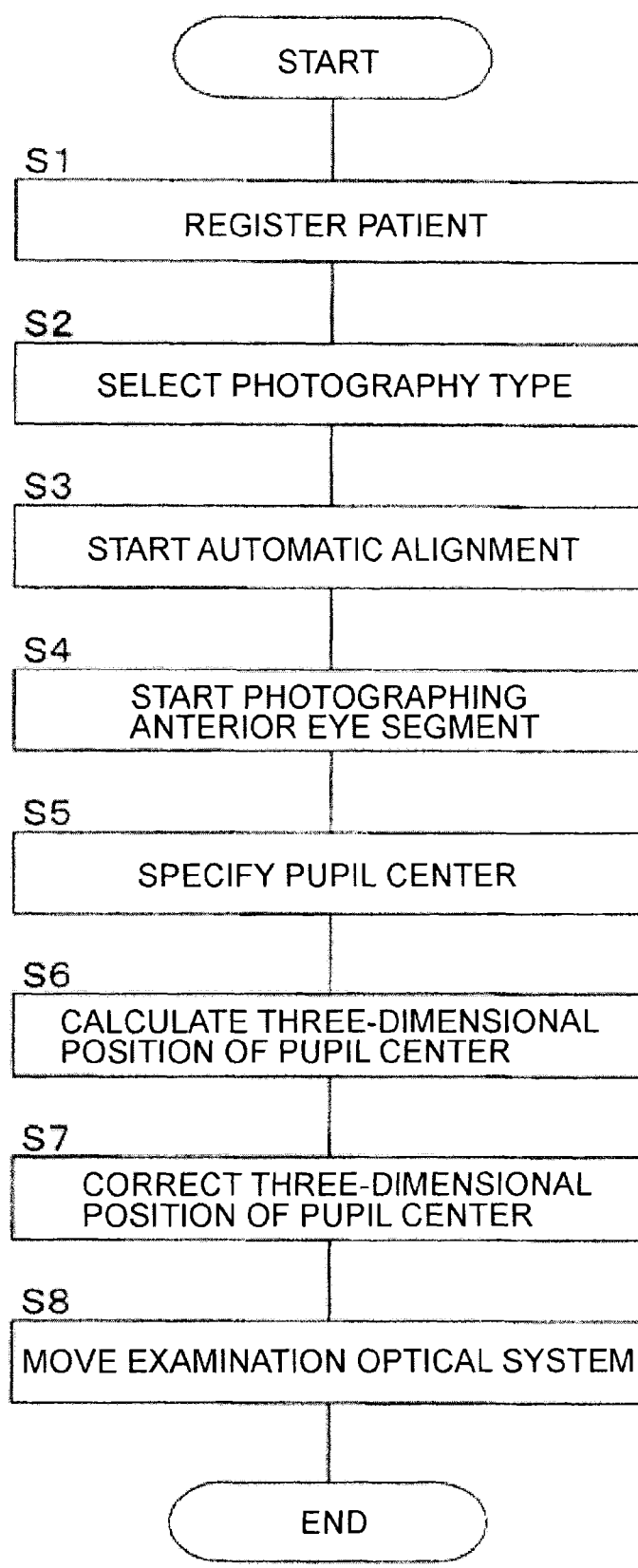
FIG. 7 is a flowchart illustrating an example of the operation of an ophthalmologic apparatus according to an embodiment.

Described below is the operation of the ophthalmologic apparatus 1. FIG. 7 illustrates an example of the operation of the ophthalmologic apparatus 1.

(S1: Register Patient)

First, the user inputs patient information on a subject using the user interface 240. The patient information may include a patient ID, patient name, and the like.

(S2: Select Photography Type)

Next, using the user interface 240, the user selects and inputs a type of photography to be performed for the subject. The items of the photography type may include, for example, photographed sites (optic disc, macula, both, etc.), the photographed eye (left eye, right eye, both eyes), image photographing pattern (only a fundus image, only an OCT image, or both), OCT scanning pattern (line scan, cross scan, radial scan, circle scan, three-dimensional scan, etc.)

(S3: Start Automatic Alignment)

Once a photography type has been selected, an instruction is given to start automatic alignment. This start instruction may be automatically issued by the controller 210 in response to the selection of the photography type in step S2 or may be manually issued by the user through the operation part 240B.

(S4: Start Photographing Anterior Eye Segment)

Having received the instruction to start the automatic alignment, the controller 210 causes the anterior eye cameras 300A and 300B to start photographing the anterior eye segment Ea. This photographing is moving image photography of the anterior eye segment Ea as a photographed object. The anterior eye cameras 300A and 300B perform moving image photography at a predetermined frame rate. Here, the timings of photographing by the anterior eye cameras 300A and 300B may be synchronized by the controller 210. The anterior eye cameras 300A and 300B successively send acquired frames to the controller 210 in real time. The controller 210 associates the frames obtained by the anterior eye cameras 300A and 300B according to the photography timing. That is, the controller 210 associates the frames acquired substantially simultaneously by both the anterior eye cameras 300A and 300B with each other. This association is performed based on, for example, the abovementioned synchronous control or based on the input timings of the frames from the anterior eye cameras 300A and 300B. The controller 210 sends a pair of associated frames to the analyzer 231.

(S5: Specify Pupil Center)

The image correction part 2311 corrects the distortion of each frame sent from the controller 210 based on the aberration information stored in the storage 212. This correction is performed in the abovementioned manner. The pair of frames with the distortion thereof corrected is sent to the characteristic point specifying part 2312.

The characteristic point specifying part 2312 analyzes each pair of frames sent from the image correction part 2311, thereby specifying a characteristic position in the frames corresponding to the center of the pupil of the anterior eye segment Ea.

A case can be considered in which the specification of a characteristic position corresponding to the pupil center fails. In such a case, it is possible to move the anterior eye cameras 300 in a direction away from the supporter 440 and/or in a direction outward of the supporter 440, and perform photography of the anterior eye segment Ea again. If an image corresponding to the anterior eye segment Ea is located at the edge of the frame, the anterior eye cameras 300 may be moved such that the anterior eye segment Ea is located in the center region of the frame.

(S6: Calculate Three-Dimensional Position of Pupil Center)

The three-dimensional position calculating part 2313 calculates the three-dimensional position of the center of the pupil of the eye E based on the positions of the anterior eye cameras 300A and 300B and the image position of the pupil center (characteristic position) specified in step S5. This process is performed in the abovementioned manner. The coordinates in the xyz coordinate system of the three-dimensional position are indicated by (x, y, z).

(S7: Correct Three-Dimensional Position of Pupil Center)

The position corrector 232 corrects the three-dimensional position of the pupil center calculated in step S6 based on the correction information 212a. This process is performed in a manner as described above. In the example of FIG. 5, by this correction process, the coordinates (x, y, z) of the pupil center calculated in step S6 are changed to (x, y, z+Δt).

(S8: Move Examination Optical System)

The controller 210 controls the optical system driver 2A based on the three-dimensional position of the pupil center corrected in step S7 to move the examination optical system. This process makes the optical axis of the examination optical system match the axis of the eye E, and makes the distance between the examination optical system and the eye E match a predetermined working distance.

For example, in the example of FIG. 5, the examination optical system is moved to such location as follows: for the xy direction, the examination optical system is moved such that the xy coordinates of its optical axis O become (x, y); for the z direction, the examination optical system is moved such that the z coordinate of the surface apex of the objective lens 22 is located away from the actual position $Q_0$ of the pupil center by WD=$WD_0$+$t_1$ in the −z direction, where $WD_0$ is a general working distance indicating the distance from the surface apex of the objective lens 22 to the anterior corneal surface Ea1 and is a predetermined value.

If the correction process of step S7 is not performed, the position of the examination optical system in the z direction is adjusted with respect to the apparent position Q of the pupil center as illustrated in FIG. 5. On the other hand, by performing the correction process, it is possible to realize the position adjustment of the examination optical system in the z direction with respect to the actual position $Q_0$ (i.e., true position) of the pupil center in real space.

Thus, the explanation of alignment in this operation example is completed.

[Actions and Effects]

Described below are actions and effects of the ophthalmologic apparatus 1.

The ophthalmologic apparatus 1 includes the examination optical system, the optical system driver 2A (drive part), the anterior eye cameras 300 (two or more imaging parts), the analyzer 231, the storage 212, the position corrector 232 (corrector), and the controller 210 (the main controller 211 in particular). The examination optical system is an optical system for examining the eye E. The optical system driver 2A moves the examination optical system. The anterior eye cameras 300 substantially simultaneously photograph the anterior eye segment Ea of the eye E from different directions. The analyzer 231 analyzes photographic images captured substantially simultaneously by the anterior eye cameras 300 to obtain the three-dimensional position of the eye E. The storage 212 stores the correction information 212a in advance. The correction information 212a is acquired based on optical properties of an eyeball and used for correcting the position of the eye E in the optical axis direction of the examination optical system. The position corrector 232 corrects the three-dimensional position of the eye E obtained by the analyzer 231 based on the correction information 212a. The controller 210 controls the optical system driver 2A based on the corrected three-dimensional position to move the examination optical system.

With the ophthalmologic apparatus 1, unlike the conventional method in which alignment (position adjustment, position matching) in the xy direction and alignment (position adjustment, position matching) in the z direction are performed individually, the three-dimensional position (xyz coordinates) of the eye E can be obtained based on two or more photographic images of the anterior eye segment Ea. This eliminates the conventional problems such as the reduction of accuracy of examination and the degradation of reproducibility due to the difference between the alignment in the xy direction and the alignment in the z direction.

Further, with the ophthalmologic apparatus 1, the three-dimensional position of the eye E thus obtained can be corrected based on the optical properties of eyeballs. Thereby, differently from conventional technologies, the z direction alignment can be achieved with high precision and accuracy without the need of additionally having a dedicated sensor. Thus, the ophthalmologic apparatus 1 is capable of performing suitable position matching between the eye and the optical system.

For example, the analyzer 231 includes the characteristic point specifying part 2312 and the three-dimensional position calculating part 2313. The characteristic point specifying part 2312 analyzes photographic images captured by the anterior eye cameras 300 to specify the position of an image corresponding to a characteristic point of the pupil or the iris. The three-dimensional position calculating part 2313 calculates the three-dimensional position of the characteristic point based on the positions of the anterior eye cameras 300 and the image position specified by the characteristic point specifying part 2312. The three-dimensional position of the characteristic point is used as the three-dimensional position of the eye E.

The correction information 212a may include the displacement Δt in the optical axis direction (z direction) of the image position of the characteristic point due to the refractive power of the anterior eye segment Ea. In this case, the position corrector 232 changes the three-dimensional position of the characteristic point calculated by the three-dimensional position calculating part 2313 by a distance corresponding to the displacement Δt. The controller 210 moves the examination optical system based on the three-dimensional position thus corrected.

The correction information 212a may include optical characteristic information that indicates measured values of optical properties of the anterior eye segment Ea of the eye E. In this case, the position corrector 232 calculates the displacement Δt of the image position due to the refractive power of the anterior eye segment Ea of the eye E based on the optical characteristic information. Further, the position corrector 232 changes the three-dimensional position of the characteristic point calculated by the three-dimensional position calculating part 2313 based on the displacement Δt. The controller 210 moves the examination optical system based on the three-dimensional position thus corrected. According to this example, position adjustment can be performed with high accuracy according to individual eyes E. Note that, in this example, the correction information 212a includes standard values of the optical properties of anterior eye segments necessary for calculating the displacement Δt.

Note that the refractive power of the anterior eye segment Ea represents the refractive power caused by tissues from the anterior surface of the cornea to the iris (the pupil), i.e., the refractive power of the cornea and that of the anterior chamber (aqueous humor).

If the characteristic point is the pupil center, the displacement Δt can be a value Δt substantially calculated by the following equations:

$$(n_1/t_1) = (n_3/f_3) - [n_3/(t_2+t_3)] \tag{1}$$

$$\Delta t = t_2 + t_3 - t_1 \tag{2}$$

where $n_1$ represents the refractive index of the air, $n_3$ represents the refractive index of the aqueous humor, $f_3$ represents the focal length of the cornea, $t_2$ represents the thickness of the cornea, and $t_3$ represents the distance between the posterior corneal surface and the pupil center.

The term "substantially" indicates the inclusion of not only the case of actually using these equations, but also the case of using available processing (e.g., real ray tracing) as an alternative of these equations.

Among the parameters used in the above equations, for at least the refractive index $n_1$ of the air, the refractive index $n_3$ of the aqueous humor, and the focal length $f_3$ of the cornea, values indicated by a model eye may be used. When these values are measured in advance, the measured values may be stored as the optical characteristic information (the correction information 212a).

For example, when the measured values (optical characteristic information) of the eye E are not used, as the refractive index $n_1$ of the air, the refractive index $n_3$ of the aqueous humor, the focal length $f_3$ of the cornea, the thickness $t_2$ of the cornea, and the distance $t_3$, values indicated by a Gullstrand eye model may be used.

When the measured values (optical characteristic information) of the eye E are used, the measured values of the thickness $t_2$ of the cornea of the eye E and/or the distance $t_3$ may be used.

When the focal length $f_3$ of the cornea is to be calculated, it may be calculated based on the refractive index $n_1$ of the air, the refractive index $n_2$ of the cornea, the refractive index $n_3$ of the aqueous humor, the thickness $t_2$ of the cornea, the curvature radius $r_1$ of the anterior corneal surface, and the curvature radius $r_2$ of the posterior corneal surface. An algorithm thereof is based on the equation for the refractive power $D_1$ of the anterior corneal surface Ea1, the equation for the refractive power $D_2$ of the posterior corneal surface Ea2, and the equation for the refractive power $D_3$ of the cornea Ea described above.

In the calculation of the focal length $f_3$ of the cornea, as at least the refractive index $n_1$ of the air, the refractive index $n_2$ of the cornea, and the refractive index $n_3$ of the aqueous humor, values indicated by a model eye may be used.

Besides, in the calculation of the focal length $f_3$ of the cornea, as the refractive index $n_1$ of the air, the refractive index $n_2$ of the cornea, the refractive index $n_3$ of the aqueous humor, the thickness $t_2$ of the cornea, the curvature radius $r_1$ of the anterior corneal surface, and the curvature radius $r_2$ of the posterior corneal surface, values indicated by a Gullstrand eye model may be used.

Further, in the calculation of the focal length $f_3$ of the cornea, as at least one of the thickness $t_2$ of the cornea, the curvature radius $r_1$ of the anterior corneal surface, and the curvature radius $r_2$ of the posterior corneal surface, a measured value of the eye E obtained in advance may be used.

<Modifications>

The embodiments described above are mere examples for embodying or carrying out the present invention, and therefore susceptible to several modifications and variations (omission, substitution, addition, etc.), all coming within the scope of the invention.

The anterior eye cameras 300 (imaging part) may be arranged below (−y direction) the lens center of the objective lens 22. With this, it is possible to reduce the possibility that the eyelid and eyelashes of a subject are caught in photographic images captured by the anterior eye cameras 300 (imaging part). Further, even if the subject has deep eye depressions (eye socket), the anterior eye segment can be suitably photographed.

In the above embodiment, two photographic images captured substantially simultaneously by the anterior eye cameras 300A and 300B may be synthesized by the image processor 230, and a composite image thus obtained may be displayed. This enables the observation of the three-dimensional form of the anterior eye segment Ea. The analysis process of the above embodiment may be performed by using the composite image.

In the above embodiment, the controller 210 is capable of displaying at least one of two photographic images captured substantially simultaneously by the anterior eye cameras 300A and 300B. This enables the observation of the morphology of the anterior eye segment Ea from different viewpoints (photographing positions).

In the above embodiment, the difference in optical path length between the optical path of the signal light LS and that of the reference light LR is varied by changing the position of the optical path length changing part 41; however, the method for changing the difference in optical path length is not limited to this. For example, a reflection mirror (reference mirror) may be arranged on the optical path of the reference light to change the optical path length of the reference light by moving the reference mirror along the traveling direction of the reference light, thereby changing the difference in optical path length. Besides, the optical path length of the signal light LS may also be changed by moving the fundus camera unit 2 and/or the OCT unit 100 relative to the eye E, thereby changing the difference in optical path length. Further, for example, if the object to be measured is not a part of a living body, the optical path length difference may be changed by moving the object to be measured in the depth direction (z direction).

In the above embodiment, while the correction information is acquired on the assumption that the principal plane position of the cornea on the object side and the image side coincides with the anterior corneal surface, the accuracy of the correction information can be improved by considering the principal plane position (principal point position). Incidentally, the principal point is the intersection of the principal plane and the optical axis.

Figure 8:
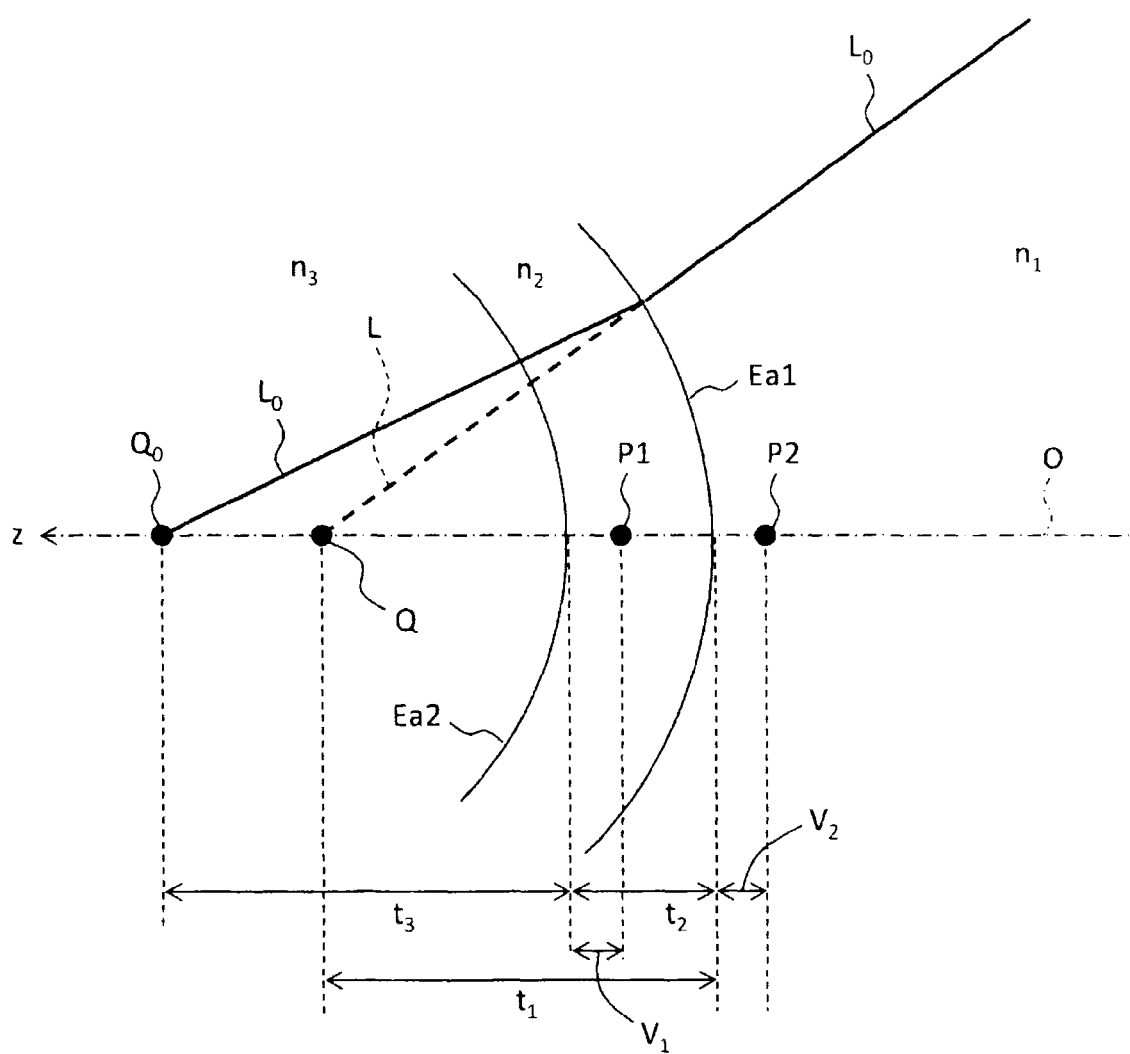
FIG. 8 is a schematic diagram for explaining a method of acquiring correction information according to a modification.

FIG. 8 illustrates an example of a method of acquiring the correction information in consideration of the principal point position. It is assumed that object-side principal point P1 is displaced from the posterior corneal surface Ea2 by $V_1$ in the −z direction, and that the image-side principal point P2 is displaced from the anterior corneal surface Ea1 by $V_2$ in the −z direction. Other reference signs are the same as those in FIG. 5.

The displacement $V_1$ of the object-side principal point P1 with respect to the posterior corneal surface Ea2 is obtained by the following equation:

$$V_1 = -(f_3/f_1)t_2$$

where $f_1$ represents the focal length of the anterior corneal surface Ea1, $f_3$ represents the focal length of the cornea Ea, and $t_2$ represents the thickness of the cornea Ea.

On the other hand, the displacement $V_2$ of the image-side principal point P2 with respect to the anterior corneal surface Ea1 is obtained in the following manner. Assuming that the refractive power of the posterior corneal surface Ea2 is $D_4$, the refractive power of the anterior corneal surface Ea1 is $D_5$, and the refractive power of the cornea Ea is $D_6$, the relationship between these powers are as follows:

$$D_4 = n_2/f_4 = (n_2 - n_3)/r_2$$

$$D_5 = n_1/f_5 = (n_1 - n_2)/r_1$$

$$D_6 = n_1/f_6 = D_4 + D_5 - (t_2/n_2)D_4 D_5$$

where $n_1$ represents the refractive index of the air, $n_2$ represents the refractive index of the cornea, $n_3$ represents the refractive index of the anterior chamber (aqueous humor). Besides, $r_1$ represents the curvature radius of the anterior corneal surface Ea1 and $r_2$ represents the curvature radius of the posterior corneal surface Ea2. Further, $f_4$ represents the focal length of the posterior corneal surface Ea2, $f_5$ represents the focal length of the anterior corneal surface Ea1, and $f_6$ represents the focal length of the cornea Ea.

Then, the displacement $V_2$ of the image-side principal point P2 with respect to the anterior corneal surface Ea1 is obtained by the following equation:

$$V_2 = -(f_6/f_4)t_2$$

where $f_4$ represents the focal length of the posterior corneal surface Ea2, $f_6$ represents the focal length of the cornea Ea, and $t_2$ represents the thickness of the cornea Ea.

From the above, the distance $t_1$ between the anterior corneal surface Ea1 and the apparent position Q of the pupil center is obtained by the following equation:

$$n_1/(t_1+V_2) = (n_3/f_3) - [n_3/(t_3-V_1)]$$

Thus, the distance $t_1$ can be obtained by the following equation:

$$t_1 = (n_1/n_3)[f_3(t_3-V_1)/(t_3-V_1-f_3)] - V_2$$

The calculation of the distance $t_1$ using this equation requires values of the parameters $n_1$, $n_3$, $f_3$, $t_3$, and $V_1$. As the values of the parameters, as in the above embodiment, it is possible to use the values of a model eye and measured values of the eye. With a Gullstrand eye model, $n_1=1$, $n_3=1.336$, $f_3=31.03$ mm, $t_3=3.1$ mm, and $V_1=-0.55$ mm. The process of obtaining the correction information from the distance $t_1$ can be performed in the same manner as in the above embodiment.

A computer program for realizing the aforementioned embodiments may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (a hard disk, a floppy (registered trade mark) disk, ZIP, etc.), and the like.

The program may be sent/received through a network such as the Internet or LAN.

What is claimed is:

1. An ophthalmologic apparatus comprising:
   an examination optical system configured to be used to examine an eye;
   a drive part configured to move the examination optical system;
   two or more imaging parts configured to substantially simultaneously photograph an anterior segment of the eye from different directions;
   an analyzer configured to analyze two or more photographic images captured substantially simultaneously by the two or more imaging parts to obtain a three-dimensional position of the eye;
   a storage configured to store correction information, acquired in advance based on optical properties of an eyeball, for a position of an eye in an optical axis direction of the examination optical system;
   a position corrector configured to correct the three-dimensional position obtained by the analyzer based on the correction information; and
   a controller configured to control the drive part based on the three-dimensional position corrected to move the examination optical system.

2. The ophthalmologic apparatus of claim 1, wherein the analyzer includes
   a characteristic point specifying part configured to analyze the two or more photographic images to specify an image position corresponding to a characteristic point of a pupil or an iris, and
   a three-dimensional position calculating part configured to calculate a three-dimensional position of the characteristic point as the three-dimensional position of the eye based on positions of the two or more imaging parts and the image position in the two or more photographic images.

3. The ophthalmologic apparatus of claim 2, wherein
   the correction information includes displacement of the image position due to refractive power of an anterior segment, and
   the position corrector is configured to correct the three-dimensional position of the characteristic point based on the displacement.

4. The ophthalmologic apparatus of claim 2, wherein
   the correction information includes optical characteristic information that indicates a measured value of an optical property of the anterior segment of the eye, and
   the position corrector is configured to calculate displacement of the image position due to refractive power of the anterior segment of the eye based on the optical characteristic information, and change the three-dimensional position of the characteristic point based on the displacement.

5. The ophthalmologic apparatus of claim 3, wherein
   the characteristic point is center of the pupil, and
   the displacement is a value substantially calculated by following equations:

$$(n_1/t_1) = (n_3/f_3) - [n_3/(t_2+t_3)]$$

$$\Delta t = t_2 + t_3 - t_1$$

where $n_1$ represents a refractive index of air, $n_3$ represents a refractive index of aqueous humor, $f_3$ represents a focal length of a cornea, $t_2$ represents a thickness of the cornea, and $t_3$ represents a distance between a posterior corneal surface and center of a pupil.

6. The ophthalmologic apparatus of claim 5, wherein at least as the refractive index $n_1$ of the air, the refractive index $n_3$ of the aqueous humor, and the focal length $f_3$ of the cornea, values indicated by a model eye are used.

7. The ophthalmologic apparatus of claim 6, wherein as the refractive index $n_1$ of the air, the refractive index $n_3$ of the aqueous humor, the focal length $f_3$ of the cornea, the thickness $t_2$ of the cornea, and the distance $t_3$, values indicated by a Gullstrand eye model are used.

8. The ophthalmologic apparatus of claim 5, wherein as the thickness $t_2$ of the cornea and/or the distance $t_3$, values obtained in advance by measuring the eye are used.

9. The ophthalmologic apparatus of claim 5, wherein the focal length $f_3$ of the cornea is calculated based on the refractive index $n_1$ of the air, the refractive index $n_2$ of the cornea, the refractive index $n_3$ of the aqueous humor, the thickness $t_2$ of the cornea, a curvature radius $r_1$ of an anterior corneal surface, and a curvature radius $r_2$ of the posterior corneal surface.

10. The ophthalmologic apparatus of claim 9, wherein as at least the refractive index $n_1$ of the air, the refractive index $n_2$ of the cornea, and the refractive index $n_3$ of the aqueous humor, values indicated by a model eye are used.

11. The ophthalmologic apparatus of claim 10, wherein as the refractive index $n_1$ of the air, the refractive index $n_2$ of the cornea, the refractive index $n_3$ of the aqueous humor, the thickness $t_2$ of the cornea, the curvature radius $r_1$ of the anterior corneal surface, and the curvature radius $r_2$ of the posterior corneal surface, values indicated by a Gullstrand eye model are used.

12. The ophthalmologic apparatus of claim 9, wherein as at least one of the thickness $t_2$ of the cornea, the curvature radius $r_1$ of the anterior corneal surface, and the curvature radius $r_2$ of the posterior corneal surface, a value obtained in advance by measuring the eye is used.

* * * * *